(12) United States Patent
Phillips et al.

(10) Patent No.: US 10,960,093 B2
(45) Date of Patent: Mar. 30, 2021

(54) LABORATORY APPARATUS COMPRISING A UV RADIATION DEVICE, AND DISINFECTION METHOD FOR A LABORATORY APPARATUS

(71) Applicant: Thermo Electron LED GmbH, Langenselbold (DE)

(72) Inventors: David Scott Phillips, Arnold, MD (US); Oliver Rupp, Langenselbold (DE)

(73) Assignee: Thermo Electron LED GmbH, Langenselbold (DE)

( * ) Notice: Subject to any disclaimer, the term of this patent is extended or adjusted under 35 U.S.C. 154(b) by 190 days.

(21) Appl. No.: 16/256,138

(22) Filed: Jan. 24, 2019

(65) Prior Publication Data

US 2019/0224351 A1    Jul. 25, 2019

(30) Foreign Application Priority Data

Jan. 24, 2018   (DE) .......................... 102018000575.6

(51) Int. Cl.
*A61L 2/10*         (2006.01)
*A61L 2/24*         (2006.01)

(52) U.S. Cl.
CPC .................. *A61L 2/10* (2013.01); *A61L 2/24* (2013.01); *A61L 2202/11* (2013.01); *A61L 2202/14* (2013.01); *A61L 2202/25* (2013.01)

(58) Field of Classification Search
CPC .......... A61L 2/10; A61L 2/24; A61L 2202/11; A61L 2202/14; A61L 2202/25
See application file for complete search history.

(56) References Cited

U.S. PATENT DOCUMENTS

| | | |
|---|---|---|
| 7,433,030 B2 | 10/2008 | Waldo et al. |
| 2008/0199353 A1 | 8/2008 | Mlodzinski et al. |
| 2009/0218512 A1 | 9/2009 | Ranta et al. |

(Continued)

FOREIGN PATENT DOCUMENTS

| | | |
|---|---|---|
| CN | 1688344 A | 10/2005 |
| CN | 101396565 A | 4/2009 |

(Continued)

OTHER PUBLICATIONS

Harrington, Brian J., PhD, MPH, et al, Monitoring Ultraviolet Lamps in Biological Safety Cabinets with Cultures of Standard Bacterial Strains on TSA Blood Agar, Mar. 2007, vol. 38 No. 3, Labmedicine, pp. 165-168.

(Continued)

*Primary Examiner* — Timothy C Cleveland
(74) *Attorney, Agent, or Firm* — Wood Herron & Evans LLP

(57) ABSTRACT

The present invention relates to a laboratory apparatus, comprising a UV radiation device which has at least one UV lamp to carry out a disinfection process, and a control device to control the UV lamp, wherein the control device is designed to specify a duration (t) during which the UV lamp is operated during the disinfection process. The control device is designed to specify the duration (t) using a control function stored in the control device as a function of the operating time (d) of the UV lamp, in such a manner that the duration (t) increases with increasing operating time (d). The present invention further relates to a method for operating such a laboratory apparatus.

12 Claims, 2 Drawing Sheets

(56) References Cited

U.S. PATENT DOCUMENTS

| | | |
|---|---|---|
| 2009/0304546 A1 | 12/2009 | Lejondahl |
| 2010/0266445 A1 | 10/2010 | Campagna |
| 2011/0172810 A1 | 7/2011 | Mlodzinski et al. |
| 2015/0060696 A1 | 3/2015 | Dayton |
| 2016/0015840 A1 | 1/2016 | Gordon |
| 2017/0263434 A1 | 9/2017 | Stibich et al. |

FOREIGN PATENT DOCUMENTS

| | | |
|---|---|---|
| CN | 201631726 U | 11/2010 |
| CN | 101217984 B | 2/2012 |
| CN | 103480019 A | 1/2014 |
| CN | 204563031 U | 8/2015 |
| CN | 105727342 A | 7/2016 |
| CN | 106806918 A | 6/2017 |
| CN | 206594558 U | 10/2017 |
| DE | 102013017377 A1 | 5/2015 |
| EP | 3269798 A1 | 1/2018 |
| GB | 2551349 A | 12/2017 |
| WO | 2017147460 A1 | 8/2017 |

OTHER PUBLICATIONS

Gostine, Andrew, M.D., MBA, et al., Evaluating the effectiveness of ultraviolet-C lamps for reducing keyboard contamination in the intensive care unit: A longitudinal analysis, American Journal of Infection Control, 44, (2016), 1089-94.

Researchgate, How much UV-light exposure time is required to disinfect a laminar flow hood?, https://www.researchgate.net/post/How_much_UV-light_exposure_time_is_required_to_disinfect_a_laminar_flow_hood?, retrieved on Jul. 10, 2018, 4 pages.

China National Intellectual Property Administration, Notification of the First Office Action, Chinese Application No. 201910065458.8, dated May 25, 2020 (6 pages).

Schneider, DWQA Questions, https://www.kois.de/ratgeber, retrieved on Jul. 10, 2018, 2 pages.

LABORATORY APPARATUS COMPRISING A UV RADIATION DEVICE, AND DISINFECTION METHOD FOR A LABORATORY APPARATUS

CROSS-REFERENCE TO RELATED APPLICATION

The present application claims priority under 35 U.S.C. § 119 of German Patent Application No. 102018000575.6, filed Jan. 24, 2018, the disclosure of which is hereby incorporated herein by reference in its entirety.

FIELD OF THE INVENTION

The present invention relates to a laboratory apparatus comprising a UV radiation device which has at least one UV lamp to carry out a disinfection process. UV radiation, especially UV-C radiation, preferably with a wavelength of 254 nm, is suitable for killing bacteria, viruses, spores, and yeasts. UV radiation is therefore frequently used for the disinfection of workspaces or laboratory equipment storage rooms used for processing or storing biological or microbiological samples.

BACKGROUND OF THE INVENTION

The period of time over which irradiation with UV radiation must take place in order to achieve sufficient disinfection depends on the size of the space to be irradiated, the type and extent of disinfection and, not least, the UV lamp which is used. A suitable irradiation period is usually determined in advance by the user of the laboratory apparatus according to the circumstances, and then input into a control device which controls the UV radiation device according to these specifications. However, it is also possible that a suitable irradiation period is determined in advance by the manufacturer of the laboratory apparatus, in the control device, which can optionally be corrected by the user.

As with other bulbs, the intensity of the radiation from UV lamps decreases continuously with increasing operating time of the lamp. There is a risk that, with increasing service life of the UV lamp, the amount of radiation is no longer sufficient to achieve the desired disinfection outcome. In order to prevent this, disinfection processes in practice are often carried out for considerably longer than would actually be necessary for a sufficient disinfection, as a precaution. For example, disinfecting processes are often allowed to run throughout the entire night. Not only does this result in significantly increased energy consumption, but also the heavy exposure to UV rays damages the components of the laboratory apparatus exposed to the radiation. Another way to prevent inadequate disinfection is early replacement of the UV lamp. The manufacturers of UV lamps usually disclose periods of operation after which the intensity of the UV radiation decreases by a certain amount, and/or a maximum period of operation after which the UV lamp should not be used any further. However, a premature replacement of the UV lamp is not only a waste of resources, but also results in considerable costs. It can also be generally contemplated that the user of the laboratory apparatus constantly checks and adjusts the required disinfection time as the operating time of the UV lamps increases. However, for the user, this is associated with considerable difficulty, and is therefore undesirable.

An object of the present invention is accordingly to provide a laboratory apparatus and a method for its operation in which the above-described problems do not occur, and which ensure a sufficient disinfection even with a longer period of operation of the at least one UV lamp in a UV radiation device without unnecessarily prolonging the disinfection time or causing additional difficulty for the user of the laboratory apparatus.

SUMMARY OF THE INVENTION

In a first aspect, the present invention thus relates to a laboratory apparatus comprising a UV radiation device, the same having at least one UV lamp for carrying out a disinfection process, and having a control device for controlling the UV lamp. The control device is designed to specify a duration during which the UV lamp is operated during the disinfection process. According to one embodiment of the present invention, the control device is further designed to specify the duration, using a control function stored in the control device, according to the operating time of the UV lamp, in such a manner that the duration increases with increasing operating time.

In the laboratory apparatus according to one embodiment of the present invention, the control device which controls the UV radiation device during the disinfection process is designed to automatically adapt the duration of the disinfection process to the operating time of the at least one UV lamp in the radiation device. The longer the at least one UV lamp has already been operated in the UV radiation device, the more the duration of the disinfection process is increased in order to compensate for the reduction in the amount of radiation emitted by the UV lamp, as is associated with a longer operating time. The manner in which this compensation takes place depends on the type of UV lamp which is used. As already described, the manufacturers of UV lamps usually indicate the decrease in the amount of radiation and/or radiation intensity along with the service life for each type of lamp, which here is equated with the operating time of the UV lamp in the UV radiation device. These manufacturer indications of decreasing irradiance can form the basis for determining the prolongation of the duration of the disinfection process. If necessary, the relationship between increasing service life and the decrease in the amount of radiation and/or radiation intensity can be determined in advance by the manufacturer of the laboratory apparatus in a known manner.

The compensation for the decreasing radiation intensity as the operating time of the at least one UV lamp increases is based on the fact that the irradiation (radiation energy/area) is the product of radiation intensity and radiation time. As such, if the radiation intensity decreases, this can be compensated for in a simple manner by prolonging the radiation time in order to ensure a consistent radiation in the laboratory apparatus. Therefore, for the UV lamp which is used, it is only necessary to determine by what factor and/or percentage the radiation intensity differs from a reference radiation intensity for different operating times in order to correct the duration in accordance with the determined deviation, specifically, for example, to multiply the irradiation time with the reciprocal value of the determined deviation factor. The reference radiation intensity can be, for example, the nominal radiation intensity of the UV lamp, which is commonly disclosed by the manufacturer of the UV lamp in the product data sheet. In accordance with the determined factor or percentage, the radiation time is prolonged for the associated operating time in such a manner that the resulting irradiation remains substantially constant. Alternatively, rather than the nominal radiation intensity, a reference radiation intensity at a specific operating time of the UV lamp can be used as a reference value, and is then defined as 100%. This can be the radiation intensity of the UV lamp when first used. It should be noted, however, that some UV lamps need a certain break-in period before they reach the intended radiation intensity. It is therefore preferred that the reference value is set only after the break-in period. Frequently, the required radiation intensity values can be taken from graphs provided by the manufacturer which depict the radiation intensity against the service life of the UV lamp.

The control device can correct the duration according to the operating time of the at least one UV lamp continuously or stepwise, by establishing a correction function in the known manner from the determined correction values, and storing this in the control device. In the case of the stepwise correction, the duration is only prolonged if certain threshold values of the operating life of the UV lamp have been reached. The duration of the disinfection process is prolonged in steps as each of the threshold values are reached. It follows that it is not necessary according to the present invention for the radiation to always exactly correspond, at increasing operating times of the at least one UV lamp, to the originally determined radiation. Rather, deviations are permissible as long as the desired disinfection result is not compromised as a result. Tolerance ranges can be used not only with a stepwise adjustment of the duration, but also for a continuous adaptation. The size of the tolerance range depends on the specific configuration of the given laboratory apparatus. However, by way of example, deviations of up to 10% from the originally determined radiation can occur, at least temporarily, wherein the deviations are preferably less than 5%, and particularly less than 2%.

During the time of operation of the at least one UV lamp, in which it is still operating at the desired radiation intensity and there has been no loss, it is not necessary to prolong the duration of the disinfection process compared to the duration originally stored in the control device. For this reason, it is preferred according to the present invention to begin the prolongation of the duration of the disinfection process only when a certain performance loss of the UV lamp has actually already taken place, or such a performance loss can be expected. This period is referred to below as the target operating time. As a rule, it can be taken from the lamp specifications available from the manufacturer, or can easily be determined by tests. The target operating time is, in particular, the period from the first use of the UV lamp in the UV radiation device up to the time at which the UV lamp emits UV radiation having a radiation intensity which just barely still corresponds to a target radiation intensity, and, in particular, the nominal radiation intensity. Until this target operating time is reached, the at least one UV lamp of the UV radiation device is operated during the disinfection process with the duration originally stored in the control device. Only after this target operating time does the control device then implement the prolongation of the duration in accordance with the above.

With the prolongation of the time carried out by the control device, according to one embodiment of the present invention as a function of the operating time of the at least one UV lamp in the UV radiation device, it is possible to reliably perform disinfection processes without premature replacement of the UV radiation device and without additional effort for the user, while also avoiding unnecessary energy consumption. The service life of the UV lamps can be exploited much better than in the prior art. However, even when the present invention is used, there is a point in time at which the radiation intensity of the UV lamp has decreased so much that reliable disinfection is no longer guaranteed. After this point in time is reached, the UV lamp should therefore be replaced. To ensure this occurs, it is preferred that a maximum operating time is stored in the control device. It corresponds in particular to the maximum service life defined by the manufacturer of the UV lamp. If the control device determines that the maximum operating time has been reached, it can, for example, output a corresponding warning to the user. This may consist of an optical and/or acoustic signal, for example, an indication in a display of the laboratory apparatus.

It is furthermore preferred that the control device is designed to carry out the prolongation of the duration in the period between the target operating time and the maximum operating time. After the maximum operating time has been reached, there is therefore no (further) prolongation of the duration of the disinfection process. This is based on the fact that an even-further prolongation of the duration can no longer ensure a reliable disinfection, because of the already significant performance loss of the UV lamp, and, therefore, also no longer makes sense. It is expedient, however, even after the maximum operating time has been exceeded, to maintain a time prolongation corresponding to that at the maximum operating time. Accordingly, a preferred cycle of a UV lamp in a laboratory apparatus according to the present invention and/or according to the inventive method is divided into three phases, with a first phase which extends to the point where the target operating time has been reached, and in which the UV lamp is operated for the originally determined duration during the disinfection process; a second phase which extends from the target operating time to the maximum operating time, and in which the duration is prolonged according to the operating time of the UV lamp in the UV radiation device; and a third phase starting from the maximum operating time, which is intended to ensure continued operation of the laboratory apparatus for a short period of time until the UV lamp has been replaced with a new UV lamp.

In principle, it is possible to implement the prolongation of the duration of the disinfecting process as a function of the operating time of the at least one UV lamp exactly in accordance with the decrease in the radiation intensity determined for each specific operating time. As already described several times, such diagrams which depict the continuous profile of the decrease in the radiation intensity over the lifetime of the lamp are available for many UV lamps. It is thus possible to use these exact values for the correction of the duration over the operating time. However, in most cases, such accuracy in implementing a disinfection process is not actually necessary, and would only result in unnecessary computational effort in the control device. It is therefore preferred according to the present invention for a linear function to be used in the calculation of the prolongation of the duration as a function of the operating time. This linear function can be determined for the UV lamp which is used from the specifications made available by the manufacturer, or by a suitable approximation of values determined on-site. One possibility is the application of a linear regression, that is, by determining a best-fit line from the available values. Instead of using the exact values, therefore, the correction factor for calculating the prolongation of the duration for each given operating time is taken from the best-fit line or calculated using a function stored for this purpose.

The linear function can also be defined only as a connection between two points. These two points may, for example, be the radiation intensities at the target operating time, on the one hand, and the maximum operating time on the other hand. The radiation intensity at the target operating time is then expediently set as 100%, and the radiation intensity at the maximum operating time is determined as x % (<100%). Between both vertices, a linear decrease of the radiation intensity is assumed. The decrease in the radiation intensity for those operating times which lie in the range between the target operating time and the maximum operating time is therefore determined in each case from the straight line which includes the values for the target operating time and the maximum operating time, and/or from the linear function by which this straight line is defined. Therefore, the correction factor for the prolongation of the duration in the period between the target operating time and the maximum operating time is determined from this linear function.

If the radiation intensity at the target operating time is denoted by $I_S$, and the radiation intensity at the maximum operating time by $I_{Max}$, with the above assumptions of a linear decrease in the radiation intensity in the range of an operating time between the target operating time $d_S$ and the maximum operating time $d_{Max}$, for any operating time $d_X$ in this range, the correction factor for the prolongation of the duration is determined by $$\left(\frac{I_S - I_{Max}}{I_S}\right)(d_x - d_s)/(d_{Max} - d_s).$$

As long as the target operating time has not yet been reached, each disinfection process is carried out with the (standard) duration $t_S$ stored in the control device. In the operating period from the target operating time $d_S$ to the maximum operating time $d_{Max}$, however, there is a prolongation of the duration using the correction factor described above, such that there is a corrected duration $t_X$ for this operating period, which is calculated according to the following formula:

$$t_x = t_s + t_s\left(\frac{I_S - I_{Max}}{I_S}\right)(d_x - d_s)/(d_{Max} - d_s)$$

This calculation formula is stored in the control device and is used when the operating time for the at least one UV lamp of the UV radiation device is in the time range between the target operating time and the maximum operating time. If more than one UV lamp is used in the UV radiation device, it makes sense to use identical lamps and to put them into operation at the same point in time, so that the same irradiation times can be implemented for all lamps of the UV radiation device.

As already described, after the maximum operating time has been reached it is expedient to not implement a further prolongation of the duration, and rather to maintain the time prolongation at the maximum operating time. At the time point $d_{Max}$, the correction factor reduces to the term $(I_S - I_{Max})/I_S$, such that the duration for the phase after the maximum operating time has been reached can be calculated as follows:

$$t_x = t_s + t_s\left(\frac{I_S - I_{Max}}{I_S}\right)$$

On the basis of the various functions for the different phases of operation, the control device controls the UV radiation device and implements an operation of the at least one UV lamp as a function of its operating time for the duration calculated in each case.

The present invention can basically be applied to any laboratory apparatus in which a UV radiation device is in use for disinfecting a workspace or storage space, or other areas of the laboratory apparatus. Apart from changes in the control device, no changes or conversions are otherwise required in the laboratory apparatus. A preferred laboratory apparatus and preferred method will be described below, by way of example. When setting up a disinfection process for the laboratory apparatus, the user proceeds in a known manner and specifies, as in the prior art, a suitable irradiation duration, taking into account the specific features of the laboratory apparatus, the type and number of UV lamps to be used, and also the contamination. This duration of the disinfection process, which corresponds to the (standard) duration $t_S$, is stored in the conventional manner in a memory of the control device. In an analogous manner, the standard irradiation duration of the disinfection process can also be determined and stored by the manufacturer or a service person entrusted with the installation and/or maintenance. In addition, a schedule can be stored in a memory of the control device which specifies at what times disinfection processes should be started. These disinfection processes can either be started automatically by the control device or the control device can issue a message, for example, by displaying it on a display of the laboratory apparatus, informing the user that a disinfection process should be started, whereupon the user then initiates the disinfection process. For this purpose, there is a timer in the control device. The timer expediently provides the date and time after which the control device can output messages relating to disinfection processes which are due, in accordance with the stored schedule, and/or can initiate these itself if necessary.

In the laboratory apparatus according to one embodiment of the present invention, the control device is also designed in such a manner that the operating time of the at least one UV lamp in the UV radiation device of the laboratory apparatus is determined and recorded by means of the timer. According to this operating time determined by the timer and stored in a memory of the control device, the control device determines, using a comparator, whether or not the at least one UV lamp has already reached the target operating time $d_S$ stored in a memory of the controller for this lamp. If this is not the case, the disinfection process is operated for a duration which corresponds to the stored (standard) duration $t_S$. The control device accordingly specifies the duration by means of a timer.

However, if the comparator of the control device determines that the stored target operating time $d_S$ for the UV lamp has been reached or already exceeded, a processor of the control device determines a corrected duration $t_X$ for the time point X determined by the timer based on the correction function stored in the memory. The stored correction function is characteristic for the UV lamp being used and is determined, as described above, in particular from the characteristic decrease in UV radiation intensity over time for this lamp type. The corresponding values can be most easily obtained from the data sheet provided by the manufacturer of this type of UV lamps, or alternatively can be determined experimentally in the known manner. It is not necessary in this case to define a separate correction function for each UV lamp which is used. Rather, one and the same correction function can be used for different UV lamps of the same type. Accordingly, it is preferred that, when several UV lamps are used for the disinfection processes of a laboratory apparatus according to the present invention, lamps of the same type are used. The control device then controls the disinfection process, either upon an automatic initiation or an initiation by a user, using the timer for the duration $t_X$, which is prolonged compared to the (standard) duration $t_S$.

The prolongation of the duration of the disinfection process according to the stored correction function takes place during an interval determined by the timer, from the target operating time $d_S$ of the at least one UV lamp to the maximum operating time $d_{Max}$. The duration of the disinfection process is prolonged, preferably linearly, for the determined UV lamp operating time, up to the maximum operating time $d_{Max}$. In this way, the required dose of UV radiation is still emitted, even though the predetermined target operating time of the UV lamp has already been exceeded and it should already have been exchanged in laboratory apparatuses of the prior art. After the maximum operating time $d_{Max}$ has been reached, sufficient UV disinfection is no longer ensured even in the laboratory apparatus according to the present invention, and the at least one UV lamp should be replaced. Thus, if the timer has transmitted a value to the control device which indicates that the maximum operating time has been exceeded, the latter issues a message to the user that the at least one UV lamp must be replaced. For safety reasons, however, the duration of the disinfection process is held constant with the previously determined maximum duration until the user has actually replaced the UV lamp(s). The replacement process can either be detected automatically by means of suitable sensors or by the user acknowledging the effected replacement via an input device coupled to the control device.

After the replacement of the at least one UV lamp, the next disinfection process begins again with the (standard) duration $t_S$, and the method described above is repeated. If another type of UV lamp is used instead of the at least one previously used UV lamp, the correction function must also be adapted accordingly to this other type of lamp. In general, different correction functions for different suitable types of UV lamps can be stored in the laboratory apparatus from the very beginning. The correct correction function must either be selected by the user in accordance with the type of lamp he is using, for which purpose a display and input device connected to the control device is expediently used, or, alternatively, it is possible to use "smart" sockets which recognize which type of lamp has been inserted into them and can transmit a corresponding message to the control device, which is processed by the latter and used for further control functions. Another possibility is to design the laboratory apparatus, for example, by using a lamp-specific socket, so that only a single type of UV lamp can be used in the laboratory apparatus, such that only a single correction function must be used.

BRIEF DESCRIPTION OF THE DRAWINGS

The present invention will be described in more detail below with reference to drawings. The drawings are merely illustrative of some preferred embodiments to which, however, the present invention is not limited. The figures are schematic. Like reference numerals designate like parts, wherein all parts are not always provided with a reference numeral. In the drawings.

DETAILED DESCRIPTION OF THE INVENTION

Figure 1:
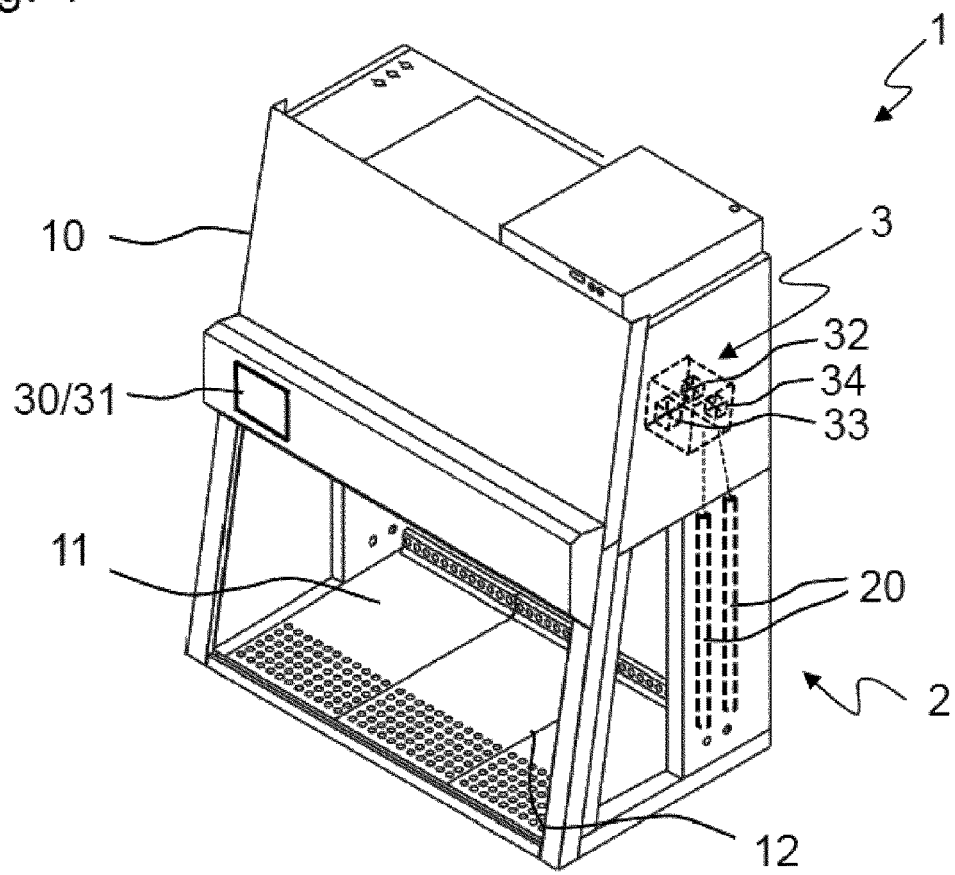
FIG. 1 shows a perspective view of a laboratory apparatus according to the present invention, using the example of a safety cabinet.

FIG. 1 shows exemplary laboratory apparatus 1 using the example of a safety cabinet. It has a housing 10 which surrounds a working space 11, which is accessible to a user via a front opening 12 which can be closed by a sliding pane. The safety cabinet is used, for example, for processing biological or microbiological samples. These can result in contamination of the working space 11. So that it is possible to kill off any germs, such as bacteria, viruses, spores, or yeasts that may have entered the working space, a UV radiation device 2 is included in the safety cabinet. In the example shown, it comprises two UV lamps 20 which are arranged on a side wall of the housing 10 on the side facing the working space 11. A control device 3, which is connected to the lamp 20, is included to control the operation of the UV radiation device 2.

Disinfection processes can be initiated from time to time by the user of the safety cabinet by inputting an appropriate command into the control device 3 via an input device 30 (in this case, a touchscreen). The control device can also be set up to remind the user at certain intervals that a disinfection process should be carried out. For example, a corresponding message is displayed on a display 31 (here in the form of a touchscreen) or a similar display device. If the user initiates a disinfection process by a corresponding input, it can be carried out immediately following the command or with a time delay, by the UV lamps 20 being operated for a predetermined duration. A timer 32 integrated in the control device 3 ensures the duration is observed. During operation, the UV lamps 20 emit UV radiation, particularly UV-C radiation, having a wavelength of 254 nm into the working space 11 of the safety cabinet 1.

The duration of the disinfection process at the beginning of the operating life of the UV lamps, which are assumed below to be the same type of lamp with the same operating time, is prespecified and stored in a memory 33 of the control device 3 by the user depending on the type of germs to be killed in the working space 11. In principle, however, it would also be possible for the manufacturer to specify a specific initial duration in the control device, which can optionally be overwritten by the user by his own input. This initial duration is valid up to a target operating time of the UV lamps and is referred to below as $t_S$.

Figure 2:
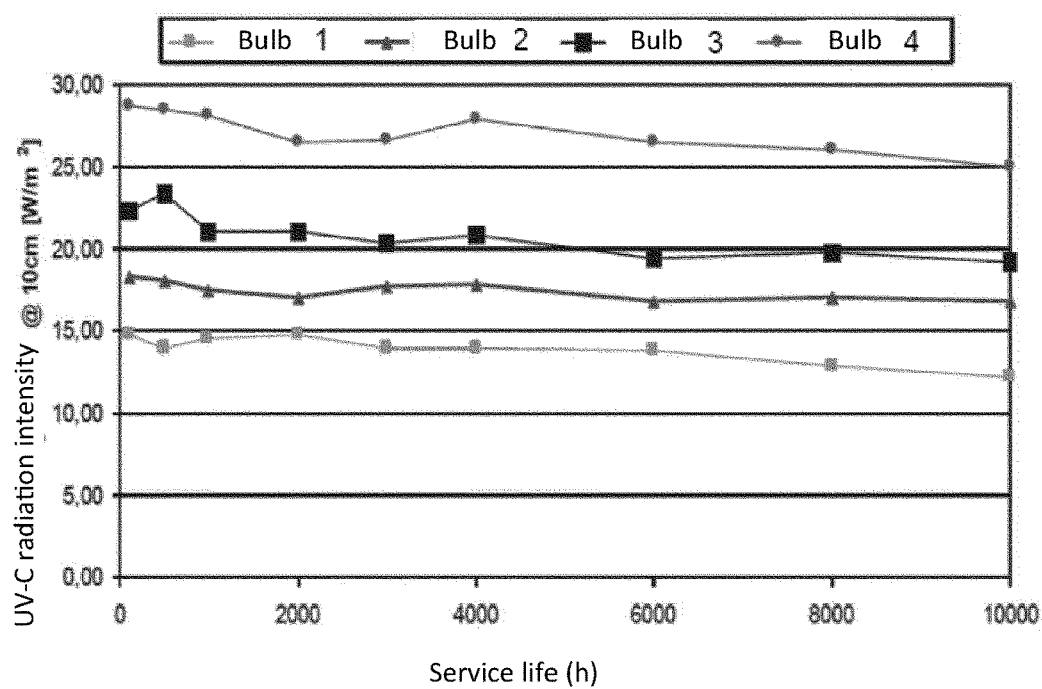
FIG. 2 shows a diagram for four different UV lamps, in which their service life is plotted against the UV-C radiation intensity.

The target operating time depends on the type of UV lamps used and denotes the operating time within which UV lamps generate the desired radiation intensity, in particular, the nominal radiation intensity, or deviate only slightly from it. The target radiation intensity can be determined inter alia from data which is usually provided by the lamp manufacturer. Alternatively, the target operating time can be determined by measurements on-site. FIG. 2 shows an example in which the target operating time is determined by utilizing a service life diagram of the lamp manufacturer. In FIG. 2, the service life is plotted in hours for four different UV lamps, which are referred to as lamp 1 to lamp 4, against the UV-C radiation intensity, each at a distance of 10 cm to the irradiated surface. The diagram thus illustrates for each lamp the change in the radiation intensity with increasing operating time. As can be seen, the radiation intensity for each of the lamps continuously decreases after a certain service life. From this point on, it is advisable to prolong the irradiation time in order to compensate for this decrease in radiation intensity and to ensure sufficient disinfection. The target operating time is set to a corresponding value.

Figure 3:
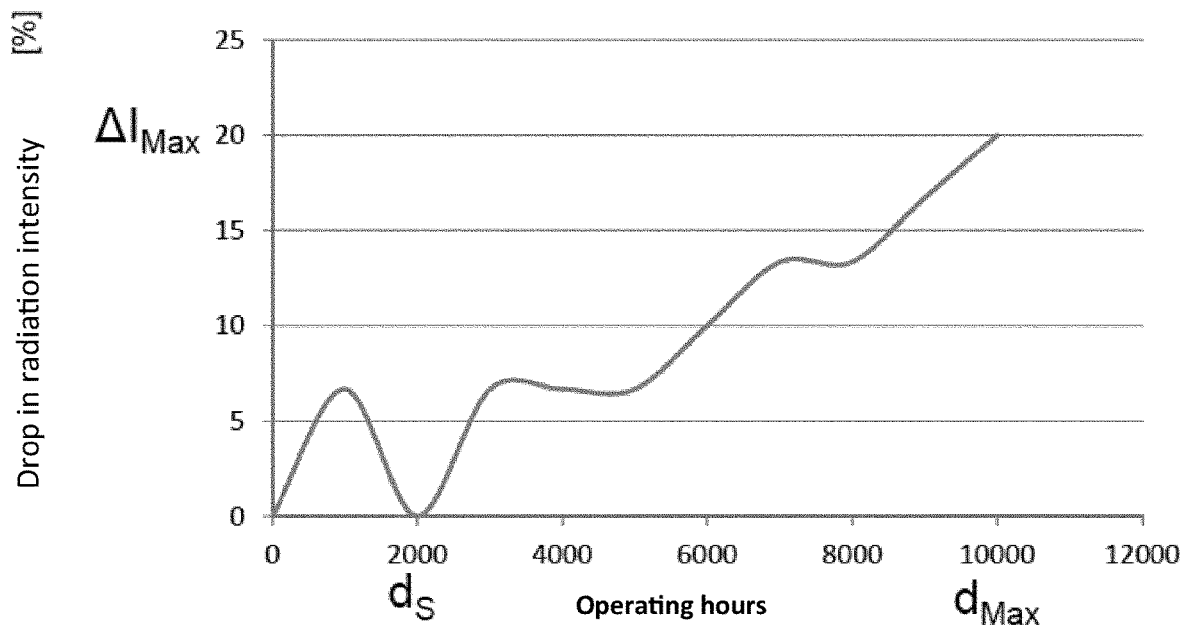
FIG. 3 shows a diagram in which, for the values of lamp 1 of FIG. 2, the operating hours are plotted against the decrease in the radiation intensity.

Below, the further procedure is described in more detail using the example of lamp 1. The profile of the radiation intensity with respect to the service life of the lamp, as shown in FIG. 2, is shown in FIG. 3 as a decrease in the radiation intensity in percent over the operating hours (the service life and/or operating time). As can be seen from the curve, the UV lamp (lamp 1) initially needs a break-in period in which the radiation intensity initially decreases, until the maximum radiation intensity has been reached after about 2000 operating hours. From that point on, the radiation intensity continues to decrease until, at an operating time of 10,000 hours, it decreases by 20% compared to the maximum radiation intensity. From this point on, it no longer makes sense to continue to operate the UV lamp. An operating time of 10,000 hours is therefore defined as the maximum operating time $d_{Max}$ of the lamp 1. The target operating time $d_S$ is set to 2000 operating hours.

According to one embodiment of a variant of the present invention, which will be described herein, the duration is prolonged to compensate for the loss of radiation intensity in the period of time between the target operating time and the maximum operating time. In principle, the profile shown in FIG. 3 could be utilized as a function for the correction of the duration. However, this would add complexity, and such high accuracy is generally not necessary in calculating the time correction. For this reason, it is preferred according to the present invention to represent the profile of the decrease in radiation intensity with respect to the operating time with a simple, linear function.

Figure 4:
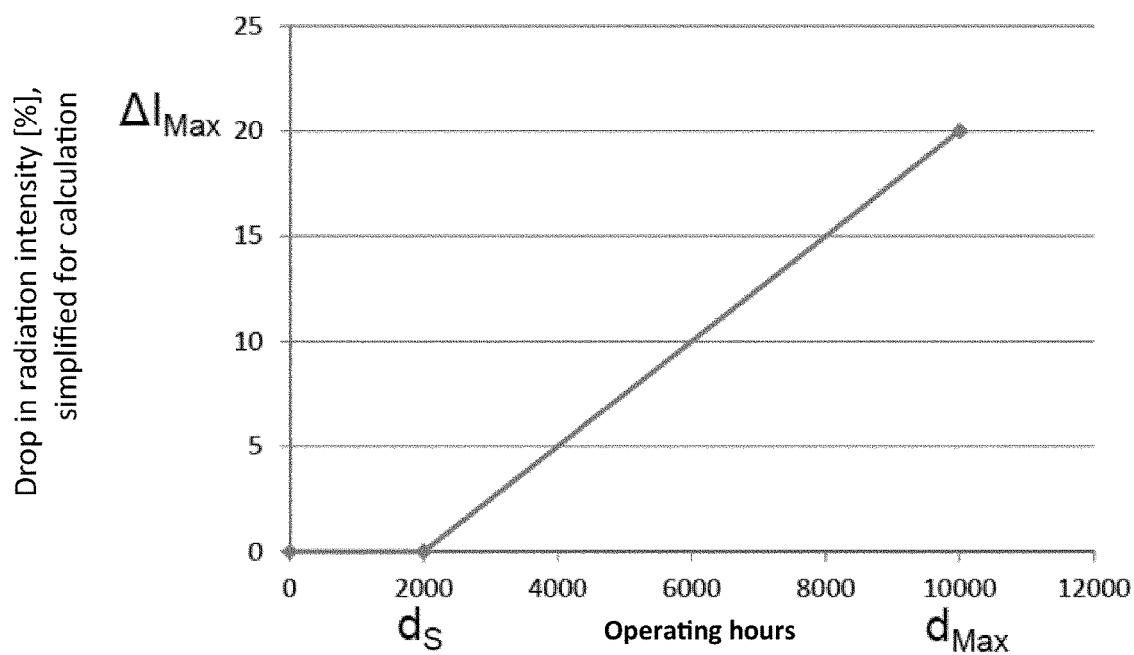
FIG. 4 shows the simplified diagram of FIG. 3 as a linear function.

This simplified relationship is shown graphically in FIG. 4. As can be seen, the function initially has a horizontal segment during an operating time from 0 to 2000 hours. In this time period, the duration of the radiation is not corrected; the duration corresponds to the prespecified duration $t_S$. At an operating time of over 2000 hours, up to the maximum operating time of 10,000 hours, on the other hand, the duration is prolonged, starting from the original duration $t_S$. For any operating time $d_X$ in the time period $d_S$ to $d_{Max}$, the relationship shown in FIG. 4 results in an associated decrease in the radiation intensity, which is to be compensated by a corresponding prolongation of the duration. The corresponding correction factor can be calculated as $$\left(\frac{I_S - I_{Max}}{I_S}\right)(d_x - d_s)/(d_{Max} - d_s)$$

where $I_S$ is the radiation intensity at the target operating time and $I_{Max}$ is the radiation intensity at the maximum operating time. The difference between $I_S$ and $I_{Max}$ is given in FIGS. 3 and 4 as $\Delta I_{Max}$ and amounts to 20% in the example, resulting in a multiplier of 0.2. This results for the operating time period from $d_S$ to $d_{Max}$ in a duration $t_X$, which is calculated according to the following formula:

$$t_x = t_s + t_s\left(\frac{I_S - I_{Max}}{I_S}\right)(d_x - d_s)/(d_{Max} - d_s)$$

Based on this calculation formula, the control device calculates the duration for which the UV lamps are operated if their operating time is in the period between the target operating time and the maximum operating time. The current operating time of the UV lamps is determined by means of a timer 34, which is integrated into the control device 3.

After the maximum operating time has been reached, the UV lamps should be replaced. To ensure this happens, the control device 3 can be designed to block any further start of a disinfection process until new UV lamps have been inserted into the UV radiation device. However, in this case there is a risk that the safety cabinet will continue to be used without disinfection, which can endanger the processed samples and the user. For this reason, it may be useful to continue to allow disinfection processes after the maximum operating time of the UV lamps has been reached. In this case, it also makes sense to continue to provide compensation for the loss of radiation intensity. In a variant of the present invention, therefore, the prolongation of the duration also takes place after the maximum duration has been exceeded, specifically, with the same correction factor that is applied for the maximum operating time. At this point, the duration accords with the formula:

$$t_x = t_s + t_s\left(\frac{I_S - I_{Max}}{I_S}\right)$$

which in the specific example means a prolongation of 0.2 $t_S$. The user is informed that the maximum operating time has been reached by the display 31 of the device (as a touch screen on the front of the housing, in this case), and he is asked to replace the UV lamps 20. Additional information on the disinfection process, for example, whether a time prolongation is already being used, and the status of the UV lamp, can also be shown on the display. The control device 3 can also be programmed to allow the user to intervene and make corrections in the process flow, such as the already-described input or change of the (standard) duration $t_S$ or the corrected duration $t_X$. The present invention ensures in the manner described that a reliable disinfection takes place without this requiring early replacement of the UV lamps, increased energy consumption, or additional difficulty for the user of the laboratory apparatus.

While the present invention has been illustrated by description of various embodiments and while those embodiments have been described in considerable detail, it is not the intention of Applicants to restrict or in any way limit the scope of the appended claims to such details. Additional advantages and modifications will readily appear to those skilled in the art. The present invention in its broader aspects is therefore not limited to the specific details and illustrative examples shown and described. Accordingly, departures may be made from such details without departing from the spirit or scope of Applicants' invention.

What is claimed is:
1. A laboratory apparatus, comprising:
a UV radiation device which has at least one UV lamp configured to carry out a disinfection process, and
a control device configured to control the at least one UV lamp, wherein the control device is designed to specify a duration (t) during which the at least one UV lamp is operated during the disinfection process, wherein the control device is designed to specify the duration (t), using a control function stored in the control device, as a function of the operating time (d) of the at least one UV lamp, in such a manner that the duration (t) increases with increasing operating time (d).

2. The laboratory apparatus according to claim 1, wherein a target operating time ($d_S$) is stored in the control device, and corresponds to an operating time in which the radiation intensity (I) essentially corresponds to a target radiation intensity ($I_S$), and the nominal radiation intensity of the at least one UV lamp, and the control device is designed to implement the prolongation of the duration (t) starting at the target operating time ($d_S$).

3. The laboratory apparatus according to claim 2, wherein a maximum operating time ($d_{Max}$) is stored in the control device, and corresponds to a maximum life defined by a manufacturer of the at least one UV lamp, and the control device is designed to implement the prolongation of the duration (t) in the period of time between the target operating time ($d_S$) and the maximum operating time ($d_{Max}$).

4. The laboratory apparatus according to claim 3, wherein the prolongation of the duration (t) as a function of the operating time (d) follows a linear function.

5. The laboratory apparatus according to claim 4, wherein the linear function is defined by the target radiation intensity ($I_S$) at the target operating time ($d_S$) being set as 100%, a maximum radiation intensity ($I_{Max}$) at the maximum operating time ($d_{Max}$) being determined as x % (<100%), and a linear reduction in the radiation intensity being assumed between the two vertices, wherein for each given operating time (d) in the range between the target operating time ($d_S$) and the maximum operating time ($d_{Max}$), a correction factor for the prolongation of the period (t) is taken from the linear function.

6. The laboratory apparatus according to claim 5, wherein the duration (t) at an operating time (x), which lies in a period of time between the target operating time ($d_S$) and the maximum operating time ($d_{Max}$), is defined by the formula $$t_x = t_s + t_s\left(\frac{I_S - I_{Max}}{I_S}\right)(d_x - d_s)/(d_{Max} - d_s)$$

where $t_S$ represents a duration set for the disinfection process when the at least one UV lamp has not yet reached the target operating time ($d_S$).

7. The laboratory apparatus according to claim 4, wherein the linear function is defined by a best-fit line which is determined from measured values of the radiation intensity in the range between the target operating time ($d_S$) and the maximum operating time ($d_{Max}$).

8. The laboratory apparatus according to claim 1, wherein the laboratory apparatus is a climate chamber comprising one of an incubator, a drying cabinet, a laboratory refrigerator, a fume hood, or a safety cabinet.

9. A method for operating a laboratory apparatus according to claim 1, wherein the control device determines, using the control function stored in the control device, the duration (t) as a function of the operating time (d) of the at least one UV lamp, wherein the duration (t) increases with increasing operating time (d), and the at least one UV radiation device carries out the disinfection process for the determined duration (t).

10. The method according to claim 9, wherein a target operating time ($d_S$) is stored in the control device, and no prolongation of the duration (t) takes place until the target operating time ($d_S$) is reached.

11. The method according to claim 9, wherein the UV radiation device, after a maximum operating time ($d_{Max}$) has been exceeded, carries out disinfection processes with the same duration (t) as calculated for the time point at the maximum operating time ($d_{Max}$) with a time corresponding to the formula $$t_x = t_s + t_s\left(\frac{I_S - I_{Max}}{I_S}\right).$$

12. The method according to claim 11, wherein when the maximum operating time is reached, a corresponding warning in the form of an optical and/or acoustic signal is output to the user.

* * * * *